United States Patent
Jeanmart et al.

(10) Patent No.: US 9,655,363 B2
(45) Date of Patent: May 23, 2017

(54) MICROBIOCIDES

(71) Applicant: Syngenta Participations AG, Basel (CH)

(72) Inventors: Stephane Andre Marie Jeanmart, Stein (CH); Damien Bonvalot, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/762,007

(22) PCT Filed: Jan. 28, 2014

(86) PCT No.: PCT/EP2014/051621
§ 371 (c)(1),
(2) Date: Jul. 20, 2015

(87) PCT Pub. No.: WO2014/118170
PCT Pub. Date: Aug. 7, 2014

(65) Prior Publication Data
US 2015/0351402 A1  Dec. 10, 2015

(30) Foreign Application Priority Data

Feb. 4, 2013 (EP) .................... 13153924

(51) Int. Cl.
*A01N 43/653* (2006.01)
*C07D 401/08* (2006.01)
*A01N 43/50* (2006.01)
*C07D 401/06* (2006.01)

(52) U.S. Cl.
CPC .......... *A01N 43/653* (2013.01); *A01N 43/50* (2013.01); *C07D 401/06* (2013.01); *C07D 401/08* (2013.01)

(58) Field of Classification Search
None
See application file for complete search history.

(56) References Cited

U.S. PATENT DOCUMENTS

| | | | |
|---|---|---|---|
| 4,616,026 A | 10/1986 | Richardson et al. | |
| 4,875,928 A | 10/1989 | Regel et al. | |
| 4,910,213 A | 3/1990 | Regel et al. | |
| 4,921,528 A | 5/1990 | Böckmann et al. | |
| 5,096,913 A * | 3/1992 | Stroech ................ | A01N 43/653 514/184 |
| 5,126,359 A | 6/1992 | Stroech et al. | |

FOREIGN PATENT DOCUMENTS

| | | |
|---|---|---|
| DE | 3422244 A1 | 12/1985 |
| EP | 0164246 A2 | 12/1985 |
| JP | 59-163374 | 9/1984 |

OTHER PUBLICATIONS

The Chemical Society of Japan, Shin-Jikken-Kagaku-Koza, 14, Synthesis and Reaction (II) of Organic Compound, Maruzen K.K., 1977, p. 755.
International Search Report for International Patent Application No. PCT/EP2014/051621 mailed Apr. 23, 2014.

* cited by examiner

*Primary Examiner* — Timothy R Rozof
(74) *Attorney, Agent, or Firm* — R. Kody Jones

(57) ABSTRACT

Compounds of formula (I) wherein the other substituents MBG, HetAr, $R^1$, $R^2$, R and $R^4$ are as defined in claim 1, and their use in compositions and methods for the control and/or prevention of microbial infection, particularly fungal infection, in plants and to processes for the preparation of these compounds.

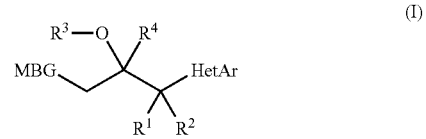

(I)

12 Claims, No Drawings

MICROBIOCIDES

RELATED APPLICATION INFORMATION

This application is a 371 of International Application No. PCT/EP2014/051621, filed 28 Jan. 2014, which claims priority to EP Patent Application No. 13153924.9, filed 04 Feb. 2013, the contents of which are incorporated herein by reference herein.

The present invention relates to novel microbiocidally active, in particular fungicidally active, cycloalkyl-heteroaryl and cycloheteroalkyl-heteroaryl containing compounds their use in compositions and methods for the control and/or prevention of microbial infection, particularly fungal infection, in plants and to processes for the preparation of these compounds.

The incidence of serious microbial infections, particularly fungal infections, either systemic or topical, continues to increase for plants.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations continues to be a major problem. Furthermore, fungicide resistance has become a serious problem, rendering these agents ineffective for some agricultural uses. As such, a need exists for the development of new fungicidal compounds.

The present invention accordingly relates to compounds of formula (I)

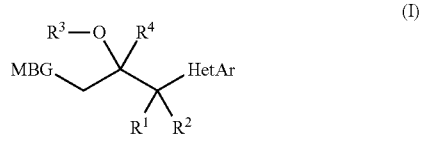

wherein

MBG is optionally substituted tetrazolyl, optionally substituted triazolyl, optionally substituted oxazolyl, optionally substituted thiazolyl, or optionally substituted imidazolyl;

HetAr is an optionally substituted monocyclic, bicyclic heteroaromatic ring or polycyclic heteroaromatic ring, $R^1$ and $R^2$ together with the carbon atoms to which they are attached form an optionally substituted 3- to 8-membered ring, optionally containing an oxygen, sulphur or nitrogen atom, $R^3$ is hydrogen, alkyl, —Si($R^5$)$_3$, —P(O)(OH)$_2$, —CH$_2$—O—P(O)(OH)$_2$, —C(O)-alkyl, —C(O)—O-alkyl, —C(O)—N-alkyl, $R^4$ is aryl, heteroaryl, alkyl or cycloalkyl each optionally substituted with 0, 1, 2 or 3 independent $R^6$;

$R^5$ is is independently alkyl or aryl $R^6$ is independently cyano, haloalkyl, hydroxy, alkoxy, halogen, or haloalkoxy;

In the substituent definitions of the compounds of the formula (I), each alkyl moiety either alone or as part of a larger group (such as alkoxy) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups. and agronomically acceptable salts, stereoisomers, diastereoisomers, enantiomers, tautomers, atriopisomers and N-oxides of those compounds.

The invention covers all agronomically acceptable salts, isomers, structural isomers, stereoisomers, diastereoisomers, enantiomers, tautomers, atropisomers and N-oxides of those compounds. The compounds of formula (I) may exist in different geometric or optical isomeric forms or in different tautomeric forms. One or more centres of chirality may be present, in which case compounds of the formula (I) may be present as pure enantiomers, mixtures of enantiomers, pure diastereomers or mixtures of diastereomers. There may be double bonds present in the molecule, such as C═C or C═N bonds, in which case compounds of formula (I) may exist as single isomers or mixtures of isomers. Centres of tautomerisation may be present. This invention covers all such isomers and tautomers and mixtures thereof in all proportions as well as isotopic forms such as deuterated compounds. Also atropisomerism may occur as a result of a restricted rotation about a single bond.

Suitable salts of the compounds of formula (I) include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In the substituent definitions of the compounds of the formula (I), each alkyl moiety either alone or as part of a larger group (such as alkoxy) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

When present, the optional substituents on heteroaromatic ring or 3- to 8-membered ring, optionally containing an oxygen, sulphur or nitrogen atom include one or more of halogen, nitro, cyano, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxy-carbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio (where the aryl group is optionally substituted), $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio (where the aryl group is optionally substituted), $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl (where the aryl group is optionally substituted), tri($C_1$-$C_4$)alkylsilyl, aryldi($C_1$-$C_4$)alkylsilyl, ($C_1$-$C_4$)alkyldiarylsilyl, triarylsilyl, aryl($C_1$-$C_4$)alkylthio($C_1$-$C_4$)alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$ alkyl)aminocarbonyl, N—($C_1$-$C_3$alkyl)-N—($C_1$-$C_3$ alkoxy)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl (where the aryl group is optionally substituted) and arylcarbonyl (where the aryl group is optionally substituted).

The preferred substituents of the substituted alkyl groups are selected from the following substituents —OH, CN, F, Cl, $C_{1-4}$alkoxy, $C_{1-4}$alkylamino. The alkyl groups are branched or linear. The most preferred alkyl groups are methyl, ethyl, propyl, iso-propyl, butyl, iso-butyl (2-methylpropyl), pentyl, 1-methylpentyl, 1-ethyl pentyl, iso-pentyl (3-methylbutyl), hexyl, heptyl, octyl, or nonyl.

Preferably the alkyl groups in the compound of formula (I) and/or the alkoxy groups in the compound of formula (I) bear not more than two further substituents, more preferably the alkyl groups in the compound of formula (I) and/or the alkoxy groups in the compound of formula (I) bear not more than one further substituent, most preferred the alkyl groups in the compound of formula (I) and/or the alkoxy groups in the compound of formula (I) are not further substituted.

Preferably, when present, the optional substituents on heteroaromatic ring or 3- to 8-membered ring, optionally containing an oxygen, sulphur or nitrogen atom include one or more of halogen, nitro, cyano, $C_1$-$C_{10}$alkoxy, $C_1$-$C_{10}$haloalkoxy, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxy-carbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy, $C_1$-$C_6$alkylsulfonyl, $C_1$-$C_6$haloalkylsulfonyl, arylsulfonyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$ alkyl)aminocarbonyl, N—($C_1$-$C_3$alkyl)-N—($C_1$-$C_3$ alkoxy)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$alkyl or halogen).

"Aryl" or "aromatic ring moiety" refers to an aromatic substituent which may be a single ring or multiple rings which are fused together, thus aryl groups derived from arenes by removal of a hydrogen atom from a ring carbon atom, and arenes are monocyclic and polycyclic aromatic hydrocarbons. The term "Aryl" may mean substituted or unsubstituted aryl unless otherwise indicated and hence the aryl moieties may be unsubstituted or substituted with one or more of the same or different substituents. Preferably aryl refers to an aromatic substituent which may be a single ring or multiple rings which are fused together, more preferably to an aromatic substituent which may be a single ring or is formed by two rings which are fused together.

Hetreoaryl signifies heteroaromatic ring system containing at least one heteroatom and consisting either of a single ring or of two or more fused rings are preferably, single rings containing up to four and bicyclic systems up to five heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, 1,3,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, preferably thiazolyl, imidazolyl, pyrrazolyl, pyridyl and pyrimidinyl.

Most preferably when present, the optional substituents on heteroaromatic ring or 3- to 8-membered ring, optionally containing an oxygen, sulphur or nitrogen atom include one or more of halogen, nitro, cyano, $C_1$-$C_6$alkoxy, $C_1$-$C_6$haloalkoxy, $C_3$-$C_6$cycloalkyl, hydroxy, $C_3$-$C_7$cycloalkyloxy, mercapto, $C_1$-$C_{10}$alkylthio.

The MBG are hereroaromatic groups as well and may therefor be substituted in the same way as the heteroaromatic rings as described in this description. Preferably MBG is optionally substituted tetrazolyl, optionally substituted triazolyl, optionally substituted oxazolyl, optionally substituted thiazolyl, or optionally substituted imidazolyl; more preferably MBG is a tetrazolyl, a triazolyl, an oxazolyl, a thiazolyl, or a imidazolyl; even more preferably MBG is a triazolyl or a imidazolyl preferably 1,2,4-triazol-1-yl or 2-imidazol-1-yl; most preferably MBG is a triazolyl especially 1,2,4-triazol-1-yl.

Halogen is fluorine, chlorine, bromine or iodine. Preferably Halogen is fluorine or chlorine.

Haloalkyl groups are alkyl groups which are substituted with one or more of the same or different halogen atoms. Therefore this definition of haloalkyl may also include perhalogenated alkyl groups. Examples of haloalkyl groups include, but are not limited $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term aryl refers to ring systems which may be mono-, bi- or tricyclic. Examples of such rings include phenyl, naphthyl, anthracenyl, indenyl or phenanthrenyl. A preferred aryl group is phenyl. Preferably aryl refers to substituted or unsubstituted pheny Cycloalkyl includes preferably cyclopropyl, cyclobutyl, cyclopentyl and cyclohexyl. Cycloalkylalkyl is preferentially cyclopropylmethyl.

Preferred values of MBG, HetAr, $R^1$, $R^2$, $R^3$, $R^4$, $R^5$ and $R^6$ are, in any combination, as set out below.

Preferably, the present invention accordingly relates to compounds of formula (I)
wherein
MBG is a tetrazolyl, a triazolyl, an oxazolyl, a thiazolyl, or a imidazolyl;
HetAr is an optionally substituted monocyclic, bicyclic heteroaromatic ring or polycyclic heteroaromatic ring,
$R^1$ and $R^2$ together with the carbon atoms to which they are attached form a 3- to 6-membered ring optionally substituted with 0, 1, 2 or 3 independent $R^6$, and optionally containing an oxygen, sulphur or nitrogen atom,
$R^3$ is hydrogen, alkyl,
$R^4$ is aryl, heteroaryl, each optionally substituted with 0, 1, 2 or 3 independent $R^6$;
$R^6$ is independently cyano, $C_1$-$C_6$haloalkyl, hydroxy, $C_1$-$C_6$alkoxy, halogen, or $C_1$-$C_6$haloalkoxy;

Most preferably, the present invention accordingly relates to compounds of formula (I) wherein
MBG is a triazolyl or a imidazolyl;
HetAr is an optionally substituted monocyclic, bicyclic heteroaromatic ring or polycyclic heteroaromatic ring,
$R^1$ and $R^2$ together with the carbon atoms to which they are attached form an optionally substituted 3- to 4-membered ring optionally substituted with 0, 1, 2 or 3 independent $R^6$, and optionally containing an oxygen
$R^3$ is hydrogen, $C_1$-$C_4$alkyl,
$R^4$ is aryl, heteroaryl, each optionally substituted with 1, 2 independent $R^6$;
$R^6$ is independently cyano, $C_1$-$C_6$haloalkyl, halogen or $C_1$-$C_6$haloalkoxy;

In a further preferred embodiment the present invention accordingly relates to compounds of formula (I) wherein
MBG is a tetrazolyl, a triazolyl, an oxazolyl, a thiazolyl, or a imidazolyl;
HetAr is a carbon attached unsubstituted or substituted 5-membered or 6-membered aromatic monocyclic ring system wherein the substituents are selected from the group consisting of halogen, cyano, nitro, hydroxy, $C_1$-$C_4$alkyl, $C_1$-$C_4$haloalkyl, $C_1$-$C_4$alkoxy, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form a 3- to 6-membered ring optionally substituted with 0, 1, 2 or 3 independent $R^6$, and optionally containing an oxygen, sulphur or nitrogen atom
$R^3$ is hydrogen, alkyl,
$R^4$ is aryl, heteroaryl, each optionally substituted with 0, 1, 2 or 3 independent $R^6$;
$R^6$ is independently cyano, $C_1$-$C_6$haloalkyl, hydroxy, $C_1$-$C_6$alkoxy, halogen, or $C_1$-$C_6$haloalkoxy;

In a further preferred embodiment the present invention accordingly relates to compounds of formula (I) wherein
MBG is a tetrazolyl, a triazolyl, an oxazolyl, a thiazolyl, or a imidazolyl;
HetAr is an unsubstituted or substituted bicyclic heteroaromatic ring wherein the substituents are selected from the group consisting of halogen, cyano, nitro, hydroxy, $C_1$-$C_4$alkyl, $C_1$-$C_4$haloalkyl, $C_1$-$C_4$alkoxy, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form a 3- to 6-membered ring optionally substituted with 0, 1, 2 or 3 independent $R^6$, and optionally containing an oxygen, sulphur or nitrogen atom
$R^3$ is hydrogen, alkyl,
$R^4$ is aryl, heteroaryl, each optionally substituted with 0, 1, 2 or 3 independent $R^6$;
$R^6$ is independently cyano, $C_1$-$C_6$haloalkyl, hydroxy, $C_1$-$C_6$alkoxy, halogen, or $C_1$-$C_6$haloalkoxy;

In a more preferred embodiment the present invention accordingly relates to compounds of formula (I) wherein
MBG is a triazolyl or a imidazolyl;
HetAr is a carbon attached unsubstituted or substituted 5-membered or 6-membered aromatic monocyclic ring system wherein the substituents are selected from the group consisting of halogen, cyano, nitro, hydroxy, $C_1$-$C_4$alkyl, $C_1$-$C_4$haloalkyl, $C_1$-$C_4$alkoxy, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form an optionally substituted 3- to 4-membered ring optionally substituted with 0, 1, 2 or 3 independent $R^6$, and optionally containing an oxygen
$R^3$ is hydrogen, $C_1$-$C_4$alkyl,
$R^4$ is aryl, heteroaryl, each optionally substituted with 1, 2 independent $R^6$;
$R^6$ is independently cyano, $C_1$-$C_6$haloalkyl, halogen or $C_1$-$C_6$haloalkoxy;

Even more preferably the present invention accordingly relates to compounds of formula (I) wherein
MBG is a triazolyl or a imidazolyl;
HetAr is an a carbon attached unsubstituted or substituted 5-membered or 6-membered aromatic monocyclic ring system wherein the substituents are selected from the group consisting of halogen, cyano, nitro, hydroxy, $C_1$-$C_4$alkyl, $C_1$-$C_4$haloalkyl, $C_1$-$C_4$alkoxy, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form an optionally substituted 3- to 4-membered ring optionally substituted with 0, 1, 2 or 3 independent $R^6$, and optionally containing an oxygen
$R^3$ is hydrogen, $C_1$-$C_4$alkyl,
$R^4$ is aryl, heteroaryl, each optionally substituted with 1, 2 independent $R^6$;
$R^6$ is independently cyano, $C_1$-$C_6$haloalkyl, halogen or $C_1$-$C_6$haloalkoxy;

Yet even more preferably the present invention accordingly relates to compounds of formula (I) wherein
MBG is a triazolyl;
HetAr is a carbon attached unsubstituted or substituted 5-membered or 6-membered aromatic monocyclic ring system wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form an optionally substituted 3- to 4-membered ring optionally substituted with 0, 1, 2 or 3 independent $R^6$, and optionally containing an oxygen
$R^3$ is hydrogen or methyl
$R^4$ is aryl, heteroaryl, each optionally substituted with 1, 2 independent $R^6$;
$R^6$ is independently $C_1$-$C_4$haloalkyl, fluorine, chlorine, $C_1$-$C_4$haloalkoxy;

In the most preferred embodiment the present invention accordingly relates to compounds of formula (I) wherein MBG is a triazolyl or imidazolyl;

HetAr is a carbon attached 6-membered aromatic monocyclic ring system containing 1 or 2 nitrogen atom wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; preferably HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$, and optionally containing an oxygen $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further preferred embodiment of the present invention accordingly relates to compounds of formula (I) wherein MBG is a triazolyl or imidazolyl;

HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl or imidazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl or imidazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl or imidazolyl;

HetAr is pyrid-2-yl wherein the substituents are selected from the group consisting of halogen, cyano, $C_1$-$C_4$haloalkyl, $C_3$-$C_8$ cycloalkyl or phenyl optionally further substituted by halogen, $C_1$-$C_4$haloalkyl, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

In the further most preferred embodiment the present invention accordingly relates to compounds of formula (I) wherein MBG is a triazolyl;

HetAr is a carbon attached 6-membered aromatic monocyclic ring system containing 1 or 2 nitrogen atom wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; preferably HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$, and optionally containing an oxygen $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further preferred embodiment of the present invention accordingly relates to compounds of formula (I) wherein MBG is a triazolyl;

HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a triazolyl;

HetAr is pyrid-2-yl wherein the substituents are selected from the group consisting of halogen, cyano, $C_1$-$C_4$haloalkyl, $C_3$-$C_8$ cycloalkyl or phenyl optionally further substituted by halogen, $C_1$-$C_4$haloalkyl, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

In the further most preferred embodiment the present invention accordingly relates to compounds of formula (I) wherein MBG is a imidazolyl;

HetAr is a carbon attached 6-membered aromatic monocyclic ring system containing 1 or 2 nitrogen atom wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; preferably HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$, and optionally containing an oxygen $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further preferred embodiment of the present invention accordingly relates to compounds of formula (I) wherein MBG is a imidazolyl;

HetAr is a carbon attached pyridyl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy; and more preferably HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a imidazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered ring optionally substituted with 0, 1, 2 or 3 independent $R^6$ $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a imidazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

A further more preferred embodiment of the present invention accordingly relates to compounds of formula (I) wherein MBG is a imidazolyl;

HetAr is pyrid-2-yl wherein the substituents are selected from the group consisting of halogen, cyano, $C_1$-$C_4$haloalkyl, $C_3$-$C_8$ cycloalkyl or phenyl optionally further substituted by halogen, $C_1$-$C_4$haloalkyl, $C_1$-$C_4$haloalkoxy;

$R^1$ and $R^2$ together with the carbon atoms to which they are attached form an optionally substituted 3- to 4-membered carbocyclic ring preferably cyclopropyl or cyclobutanyl $R^3$ is hydrogen or methyl $R^4$ is aryl, optionally substituted with 1, 2 independent $R^6$;

$R^6$ is independently $C_1$-$C_4$haloalkyl, fluorine, chlorine, $C_1$-$C_4$haloalkoxy;

In one embodiment the compounds of the present invention are selected from 1-(4-chlorophenyl)-1-[1-(2-pyridyl)cyclopropyl]-2-(1,2,4-triazol-1-yl)ethanol, 1-[1-(5-bromo-3-chloro-2-pyridyl)cyclopropyl]-1-(4-fluorophenyl)-2-(1,2,4-triazol-1-yl)ethanol, 1-[1-(5-bromo-2-pyridyl)cyclopropyl]-1-(4-fluorophenyl)-2-imidazol-1-yl-ethanol, 1-[1-(5-bromo-2-pyridyl)cyclopropyl]-1-(4-fluorophenyl)-2-(1,2,4-triazol-1-yl)ethanol, 1-[1-(5-bromo-3-chloro-2-pyridyl)cyclopropyl]-1-(4-fluorophenyl)-2-imidazol-1-yl-ethanol, 1-[1-[5-bromo-6-(4-fluorophenyl)-2-pyridyl]cyclopropyl]-1-(4-fluorophenyl)-2-(1,2,4-triazol-1-yl)ethanol, 1-[1-(5-cyclopropyl-2-pyridyl)cyclopropyl]-1-(4-fluorophenyl)-2-(1,2,4-triazol-1-yl)ethanol, 4-[6-[1-[1-(4-fluorophenyl)-1-hydroxy-2-(1,2,4-triazol-1-yl)ethyl]cyclopropyl]-3-pyridyl]benzonitrile, 1-[1-(6-chloro-3-pyridyl)cyclopropyl]-1-(4-fluorophenyl)-2-(1,2,4-triazol-1-yl)ethanol, 1-(4-fluorophenyl)-1-[1-(2-pyridyl)cyclopropyl]-2-(1,2,4-triazol-1-yl)ethanol, 1-(4-chlorophenyl)-1-[1-(5-chloro-2-pyridyl)cyclopropyl]-2-(1,2,4-triazol-1-yl)ethanol, 6-[1-[1-(4-fluorophenyl)-1-hydroxy-2-(1,2,4-triazol-1-yl)ethyl]cyclopropyl]pyridine-3-carbonitrile, 1-(4-fluorophenyl)-2-(1,2,4-triazol-1-yl)-1-[1-[5-(trifluoromethyl)-2-pyridyl]cyclopropyl]ethanol, 1-[1-(5-chloro-2-pyridyl)cyclopropyl]-1-(4-fluorophenyl)-2-(1,2,4-triazol-1-yl)ethanol, 1-(4-chlorophenyl)-1-[1-(2-pyridyl)cyclopentyl]-2-(1,2,4-triazol-1-yl)ethanol, 1-(4-chlorophenyl)-1-[1-(5-chloro-2-pyridyl)cyclobutyl]-2-(1,2,4-triazol-1-yl)ethanol, 1-[1-(5-bromo-2-pyridyl)cyclobutyl]-1-(4-fluorophenyl)-2-(1,2,4-triazol-1-yl)ethanol, 1-(4-fluorophenyl)-2-(1,2,4-triazol-1-yl)-1-[1-[5-[3-(trifluoromethoxy)phenyl]-2-pyridyl]cyclobutyl]ethanol and 1-[1-[5-(4-chloro-2-fluoro-phenyl)-2-pyridyl]cyclobutyl]-1-(4-fluorophenyl)-2-(1,2,4-triazol-1-yl)ethanol.

In one embodiment the compounds of the present invention relates to 1-(4-chlorophenyl)-1-[1-(2-pyridyl)cyclopropyl]-2-(1,2,4-triazol-1-yl)ethanol.

In one embodiment the compounds of the present invention relates to 1-[1-(5-bromo-3-chloro-2-pyridyl)cyclopropyl]-1-(4-fluorophenyl)-2-(1,2,4-triazol-1-yl)ethanol.

In one embodiment the compounds of the present invention relates to 1-[1-(5-bromo-2-pyridyl)cyclopropyl]-1-(4-fluorophenyl)-2-imidazol-1-yl-ethanol.

In one embodiment the compounds of the present invention relates to 1-[1-(5-bromo-2-pyridyl)cyclopropyl]-1-(4-fluorophenyl)-2-(1,2,4-triazol-1-yl)ethanol.

In one embodiment the compounds of the present invention relates to 1-[1-(5-bromo-3-chloro-2-pyridyl)cyclopropyl]-1-(4-fluorophenyl)-2-imidazol-1-yl-ethanol.

In one embodiment the compounds of the present invention relates to 1-[1-[5-bromo-6-(4-fluorophenyl)-2-pyridyl]cyclopropyl]-1-(4-fluorophenyl)-2-(1,2,4-triazol-1-yl)ethanol.

In one embodiment the compounds of the present invention relates to 1-[1-(5-cyclopropyl-2-pyridyl)cyclopropyl]-1-(4-fluorophenyl)-2-(1,2,4-triazol-1-yl)ethanol.

In one embodiment the compounds of the present invention relates to 4-[6-[1-[1-(4-fluorophenyl)- In one embodiment the compounds of the present invention relates to 1-hydroxy-2-(1,2,4-triazol- In one embodiment the compounds of the present invention relates to 1-yl)ethyl]cyclopropyl]-3-pyridyl]benzonitrile.

In one embodiment the compounds of the present invention relates to 1-[1-(6-chloro-3-pyridyl)cyclopropyl]-1-(4-fluorophenyl)-2-(1,2,4-triazol-1-yl)ethanol.

In one embodiment the compounds of the present invention relates to 1-(4-fluorophenyl)-1-[1-(2-pyridyl)cyclopropyl]-2-(1,2,4-triazol-1-yl)ethanol.

In one embodiment the compounds of the present invention relates to 1-(4-chlorophenyl)-1-[1-(5-chloro-2-pyridyl)cyclopropyl]-2-(1,2,4-triazol-1-yl)ethanol.

In one embodiment the compounds of the present invention relates to 6-[1-[1-(4-fluorophenyl)-1-hydroxy-2-(1,2,4-triazol-1-yl)ethyl]cyclopropyl]pyridine-3-carbonitrile.

In one embodiment the compounds of the present invention relates to 1-(4-fluorophenyl)-2- In one embodiment the compounds of the present invention relates to (1,2,4-triazol-1-yl)-1-[1-[5-(trifluoromethyl)-2-pyridyl]cyclopropyl]ethanol.

In one embodiment the compounds of the present invention relates to 1-[1-(5-chloro-2-pyridyl)cyclopropyl]-1-(4-fluorophenyl)-2-(1,2,4-triazol-1-yl)ethanol.

In one embodiment the compounds of the present invention relates to 1-(4-chlorophenyl)-1-[1-(2-pyridyl)cyclopentyl]-2-(1,2,4-triazol-1-yl)ethanol.

In one embodiment the compounds of the present invention relates to 1-(4-chlorophenyl)-1-[1-(5-chloro-2-pyridyl)cyclobutyl]-2-(1,2,4-triazol-1-yl)ethanol.

In one embodiment the compounds of the present invention relates to 1-[1-(5-bromo-2-pyridyl)cyclobutyl]-1-(4-fluorophenyl)-2-(1,2,4-triazol-1-yl)ethanol.

In one embodiment the compounds of the present invention relates to 1-(4-fluorophenyl)-2-(1,2,4-triazol-1-yl)-1-[1-[5-[3-(trifluoromethoxy)phenyl]-2-pyridyl]cyclobutyl]ethanol.

In one embodiment the compounds of the present invention relates to 1-[1-[5-(4-chloro-2-fluoro-phenyl)-2-pyridyl]cyclobutyl]-1-(4-fluorophenyl)-2-(1,2,4-triazol-1-yl)ethanol.

Further preferred embodiments of the present invention are the embodiments E1 to E11, which are defined as compounds of formula I which are represented by one formula selected from the group consisting of the formulae T-1 to T-11 as described below, wherein in formulae T-1 to T-11 the meanings of the substituents HetAR and $R^3$ have the preferred meanings as mentioned above.

For example, embodiment E1 is represented by the compounds of formula T-1

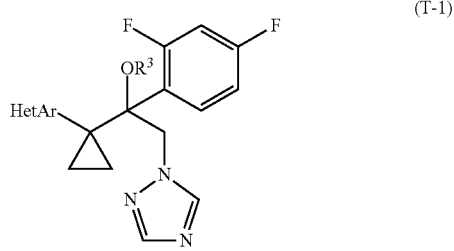

(T-1)

and the substituents HetAR and $R^3$ have the meanings as defined above.

Embodiments E2 to E11 are defined accordingly and the substituents HetAR and $R^3$ have the meanings as defined above.

Those skilled in the art will appreciate that compounds of formula (I) may contain an heteroaromatic moiety bearing one or more substituents capable of being transformed into alternative substituents under known conditions, and that these compounds may themselves serve as intermediates in the preparation of additional compounds of formula (I).

For example, compounds of formula (I) wherein HetAr is optionally substituted heteroaryl substituted by an halogen, preferably bromide or iodine, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Compounds of formula (I) may be prepared according to the process outlines in scheme 1 below:

Scheme 1

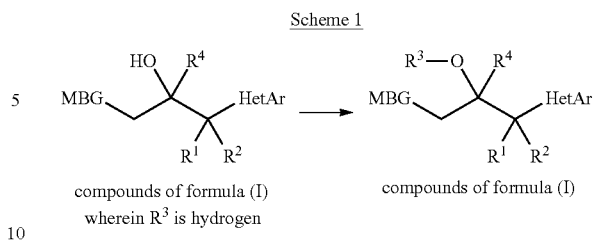

compounds of formula (I)
wherein $R^3$ is hydrogen compounds of formula (I)

Accordingly, compounds of formula (I) may be prepared by treating compounds of formula (I) wherein $R^3$ is hydrogen with an alkylating agent or a silylating agent in the presence of suitable selected inorganic base such as sodium hydride or potassium tert-butoxide and the like; in a suitable organic solvent like acetonitrile or tetrahydrofuran at a temperature between −30° C. and 200° C. For related example, see JP60172904.

Compounds of formula (I) wherein $R^3$ is hydrogen may be prepared according to the process outlines in scheme 2 below:

Scheme 2

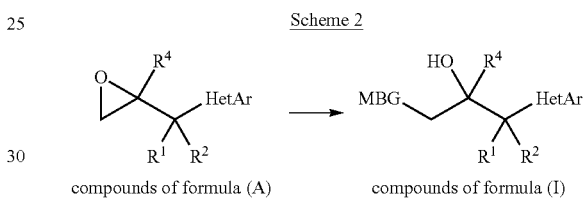

compounds of formula (A)

compounds of formula (I)

Accordingly, compounds of formula (I) wherein $R^3$ is hydrogen may be prepared by treating compounds of formula (A) with a triazole, an imidazole or a tetrazole in the presence of suitable selected inorganic base such as potassium carbonate and the like; in a suitable organic solvent like acetonitrile or dimethylforamide at a temperature between −30° C. and 200° C. For examples of similar transformation, see Capriati, V. et al. Org. Lett. 2002, 4(14), 2445; Ogata, M. et al. J. Med. Chem. 1987, 30, 1054.

Compounds of formula (A) may be prepared by the addition of an alkyl sulfonium or sulfoxonium salt, such as trimethylsulfonium iodide, trimethylsulfoxonium iodide onto compounds of formula (B) in the presence of a base such as sodium hydride in a suitable solvent such as dimethyl sulfoxide at a temperature between 0° C. and 50° C. as described in scheme 3. For example of analogous method see Corey E. J. and Chaykovsky M. J. Am. Chem. Soc. 1965, 87, 1353; Corey E. J. et al. Tetrahedron Lett. 1967, 2325.

Scheme 3

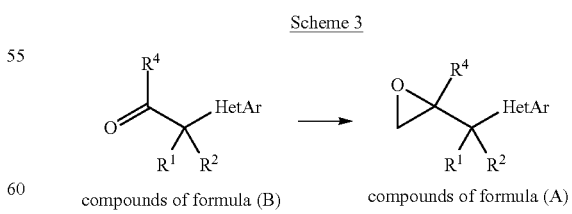

compounds of formula (B)

compounds of formula (A)

Compounds of formula (B) may be prepared by the addition of compounds of formula (D) to compounds of formula (C) in a suitable solvent such as tetrahydrofuran at a temperature between 0° C. and 50° C. as described in scheme 4.

Scheme 4

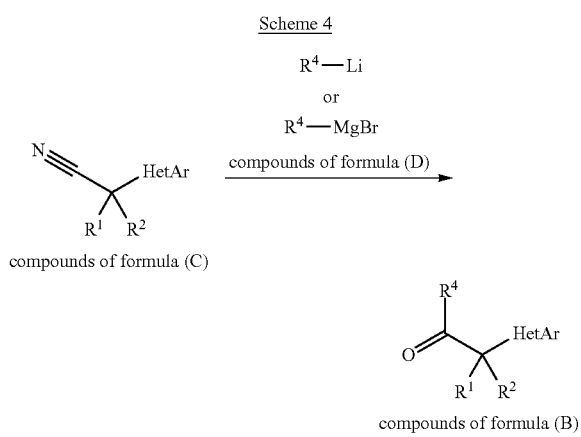

Compounds of formula (D) are known or may be made from known compounds by known methods.

Compounds of formula (C) are known or may be made from known compounds by known methods. For example see Pauls, H. W. et al. WO2013053051; Klapars, A. et al. *J. Org. Chem.* 2005, 70(24), 10186; Thompson, A. D. and Haestis, M. P. *J. Org. Chem.* 2013, 78(2), 762.

Scheme 5

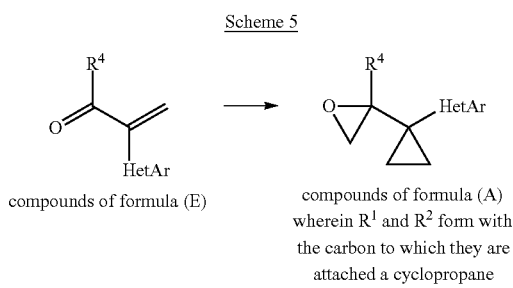

compounds of formula (E)

compounds of formula (A) wherein $R^1$ and $R^2$ form with the carbon to which they are attached a cyclopropane Alternatively, compounds of formula (A) wherein $R^1$ and $R^2$ form with the carbon to which they are attached a cyclopropane may be prepared by the reaction of compounds of formula (E) with by the addition of an alkyl sulfonium or sulfoxonium salt, such as trimethylsulfonium iodide, trimethylsulfoxonium iodide onto compounds of formula (B) in the presence of a base such as sodium hydride in a suitable solvent such as dimethyl sulfoxide at a temperature between 0° C. and 50° C. as described in scheme 5. For example of analogous procedure see By Wagner, G. et al *Zeitschrift fuer Naturforschung, B: Chemical Sciences* 2001, 56(1), 25-38.

Compounds of formula (E) are known or may be made from known compounds by known methods. For example see Renga, J. M. et al. *Org. Proc. Res. Dev.* 2003, 7, 267.

It has now been found that the compounds of formula (I) according to the invention have, I for practical purposes, a very advantageous spectrum of activities for protecting useful plants against diseases that are caused by phytopathogenic microorganisams, such as fungi, bacteria or viruses.

The invention therefore also relates to a method of controlling or preventing infestation of useful plants by phytopathogenic microorganisms, wherein a compound of formula (I) is applied as active ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore, the compounds of formula (I) according to the invention may be used for controlling fungi in related areas, for example in the protection of technical materials, including wood and wood related technical products, in food storage or in hygiene management.

The compounds of formula (I) are, for example, effective against the phytopathogenic fungi of the following classes: *Fungi imperfecti* (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the *Ascomycetes* classes (e.g. *Venturia* and *Erysiphe, Podosphaera, Monilinia, Uncinula*) and of the *Oomycetes* classes (e.g. *Phytophthora, Pythium, Plasmopara*). Furthermore, the novel compounds of formula (I) are effective against phytopathogenic bacteria and viruses (e.g. against *Xanthomonas* spp, *Pseudomonas* spp, *Erwinia amylovora* as well as against the tobacco mosaic virus). The compounds of formula (I) are also effective against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain *Lepidoptera*, include the European corn borer.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) or compositions, comprising a compound of formula (I) as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as active ingredient and an inert carrier, is foliar application. The frequency of application and the rate of application will depend on the risk of infestation by the corresponding pathogen. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant or, if desired as well, a further, other biocidally active ingredient, is prepared in a known manner, typically by intimately mixing and/or grinding the compound with extenders, for example solvents, solid carriers and, optionally, surface-active compounds (surfactants).

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and *Bacillus thuringiensis* preparations.

The following mixtures of the compounds of formula I with active ingredients are preferred (the abbreviation "TX" means "one compound according to the formula (I) or one specific compound selected from the Table 1 to 22 or a specific compound selected from Table T1 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056),+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin)oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, Myrothecium verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and Reynoutria sachalinensis extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfo-carb [66952-49-6]+TX, metrafenone

[220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, N-cyclopropyl-3-(difluoromethyl)-5-fluoro-1-methyl-N-[[2-(1-methylethyl)phenyl]methyl]-1H-Pyrazole-4-carboxamide (CAS Registry Number: 1255733-83-5)+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-(difluoromethyl)-N-methoxy-1-methyl-N-[1-methyl-2-(2,4,6-trichlorophenyl)ethyl]-1H-Pyrazole-4-carboxamide+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, (S)-[3-(4-Chloro-2-fluoro-phenyl)-5-(2,4-difluoro-phenyl)-isoxazol-4-yl]-pyridin-3-yl-methanol+TX, 3-(4-Chloro-2-fluoro-phenyl)-5-(2,4-difluoro-phenyl)-isoxazol-4-yl]-pyridin-3-yl-methanol+TX, (3-difluoromethyl-1-methyl-1H-pyrazole-4-carboxylic acid (3',4'-dichloro-5-fluoro-1,1'-biphenyl-2-yl)-amide (bixafen)+TX, (N-{2-[3-Chloro-5-(trifluoromethyl)pyridin-2-yl]ethyl}-2-(trifluoromethyl)benzamid (fluopyram)+TX, N-[2-(1,3-dimethylbutyl)phenyl]-5-fluoro-1,3-dimethyl-1H-pyrazole-4-carboxamide (Penflufen)+TX, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (CAS Reg. No.: 1003318-67-9, oxathiapiprolin)+TX and 3-difluoromethyl-1-methyl-1H-pyrazole-4-carboxylic acid (3',4',5'-trifluoro-biphenyl-2-yl)-amide (dislosed in WO 2006/087343)+TX, flupyradifurone (CAS registry number 951659-40-8)+TX, afidopyropen (CAS registry number 915972-17-7)+TX, *pasteuria penetrans* and TX, *pasteuria* spp. +TX, *bacillus firmus*+TX, *bacillus cereus*+TX, *bacillus subtilis*+TX, *pasteuria penetrans*+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of one compound according to the formula (I) or one specific compound selected from the Table 1 to 22 or a specific compound selected from Table T1 of the present invention and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on the other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising one compound according to the formula (I) or one specific compound selected from the Table 1 to 22 or a specific compound selected from Table T1 of the present invention and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the one compound according to the formula (I) or one specific compound selected from the Table 1 to 22 or a specific compound selected from Table T1 of the present invention and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

The following non-limiting examples illustrate the above-described invention in greater detail without limiting it.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

EXAMPLE 1

Synthesis of 1-(4-chlorophenyl)-1-[1-(2-pyridyl)cyclopropyl]-2-(1,2,4-triazol-1-yl)ethanol

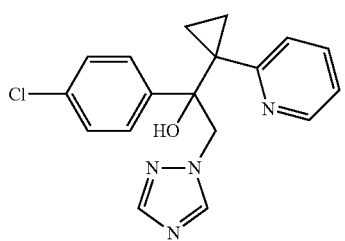 [SMILES: OC(Cn1cncn1)(c1ccc(Cl)cc1)C1(c2ccccn2)CC1]

Step 1: Synthesis of 1-(2-pyridyl)cyclopropanecarbonitrile

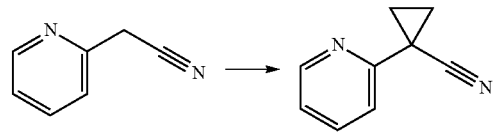 [SMILES: N#CCc1ccccn1 ; N#CC1(c2ccccn2)CC1]

An aqueous solution of sodium hydroxide (40 mL, 7.5 M) was added to a solution of 2-(2-pyridyl)acetonitrile (3.00 g, 25.4 mmol), 1,2-dibromomethane (4.77 g, 25.4 mmol) and tetrabutylammonium chloride (7.08 g, 25.4 mmol) in acetonitrile (40 mL) at room temperature. The resulting mixture was stirred at room temperature for four hours and then extracted with ethyl acetate (2×50 mL). The combined extracts were washed with brine (1×40 mL), dried over magnesium sulphate and filtered. The solvents were removed under reduced pressure and the residue was purified by flash chromatography to give 1,7 g of 1-(2-pyridyl)cyclopropanecarbonitrile as a white solid.

Step 2: Synthesis of (4-chlorophenyl)-[1-(2-pyridyl)cyclopropyl]methanone

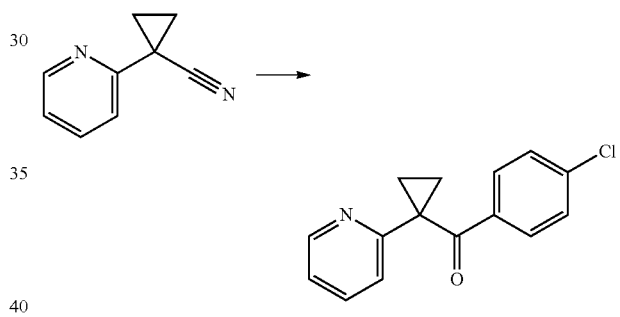

To a solution of 1-(2-pyridyl)cyclopropanecarbonitrile (500 mg, 3.47 mmol) in tetrahydrofuran (10 mL) was slowly added the bromo-(-4chlorophenyl)magnesium (3.8 ml, 1M in THF, 3.8 mmol) at 0° C. The reaction mixture was stirred for one hour at 0° C. and then let warm to room temperature and stirred overnight. The reaction mixture was quenched with 0.5 M hydrochloric acid (20 mL) and then extracted with ethyl acetate (2×40 mL). The combined layers were washed with brine (1×40 mL), dried over magnesium sulphate, filtered and the concentrated under reduced pressure. The crude product was purified by flash chromatography to give 0.89 g of (4-chlorophenyl)-[1-(2-pyridyl)cyclopropyl]methanone.

Step 3: Synthesis of 2-[1-[2-(4-chlorophenyl)oxiran-2-yl]cyclopropyl]pyridine

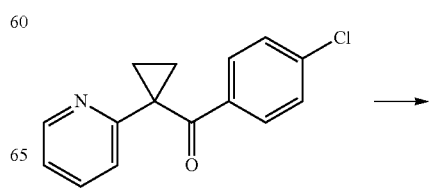

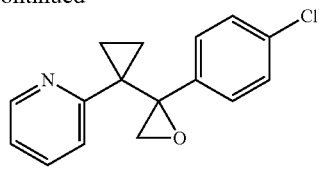

Sodium hydride (60% dispersion in mineral oil, 70 mg, 1.75 mmol) was placed under nitrogen and then dimethyl sulfoxide (5 mL) was added. Trimethylsulfonium iodide (360 mg, 1.75 mmol) was added as a solid after 15 minutes followed, after a further 30 minutes by (4-chlorophenyl)-[1-(2-pyridyl)cyclopropyl]methanone (410 mg, 1.59 mmol). The reaction mixture was stirred at room temperature for 24 hours and then diluted with ethyl acetate (30 mL). The reaction mixture was washed with water (15 mL) and brine (15 mL). The organic phase was dried over magnesium sulphate, filtered and concentrated under reduced pressure to give the crude product. The crude product was purified by flash chromatography to give the desired product with an unknown material. This was used as such into the next step.

Step 4: Synthesis of 1-(4-chlorophenyl)-1-[1-(2-pyridyl)cyclopropyl]-2-(1,2,4-triazol-1-yl)ethanol

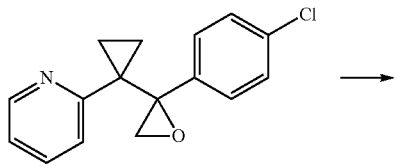

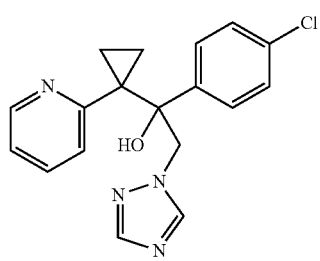

Potassium carbonate (195 mg, 1.93 mmol), 1,2,4-triazole (134 mg, 1.93 mmol) and 2-[1-[2-(4-chlorophenyl)oxiran-2-yl]cyclopropyl]pyridine (350 mg, 1.29 mmol) were all mixed together in dmethyl foramide (10 mL) and stirred overnight at 60° C. 20 mL of water and 20 mL of ethyl acetate were added and the organic layer was separated. The organic phase was washed with brine (10 mL), dried over magnesium sulphate, filtered and evaporated under reduced pressure to give the crude product. The crude product was purified by flash chromatography to give 1-(4-chlorophenyl)-1-[1-(2-pyridyl)cyclopropyl]-2-(1,2,4-triazol-1-yl)ethanol.

EXAMPLE 2

Preparation of 1-(4-fluorophenyl)-2-(1,2,4-triazol-1-yl)-1-[1-[5-(trifluoromethyl)-2-pyridyl]cyclopropyl]ethanol

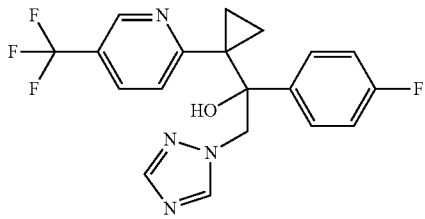 [SMILES: OC(Cn1cncn1)(c1ccc(F)cc1)C1(c2ccc(C(F)(F)F)cn2)CC1]

Step 1: Synthesis of 1-(4-fluorophenyl)-2-[5-(trifluoromethyl)-2-pyridyl]ethanone

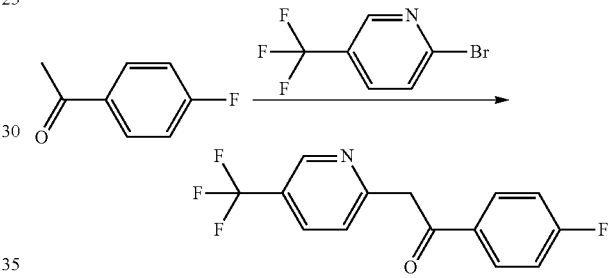

Sodium hydride (60% dispersion in mineral oil, 796 mg, 19.9 mmol) was dispersed in tetrahydofuran (15 ml) and heated to 55° C. under mechanical stirring. A solution of 1-(4-fluorophenyl)ethanone (1.83 g, 13.3 mmol) and 2-bromo-5-(trifluoromethyl)pyridine (3.00 g, 13.3 mmol) in tetrahydrofuran (15 ml) was added over a 10 minutes period. After an additional ten hours at reflux, the mixture was cooled to 0° C., and excess sodium hydride was quenched via addition of a solution of methanol in diethylether over 1 hour. The mixture was partitioned between ether (25 ml) and brine (25 ml). The organic layer was washed with brine (25 ml). The combined aqueous layers were washed with diethyl ether (25 ml). The combined diethylether layers were dried over sodium sulphate, filtered, and evaporated under reduced pressure to a dark solid which was then purified by flash chromatography to yield 1.93 g of 1-(4-fluorophenyl)-2-[5-(trifluoromethyl)-2-pyridyl]ethanone.

Step 2: Synthesis of 1-(4-fluorophenyl)-2-[5-(trifluoromethyl)-2-pyridyl]prop-2-en-1-one

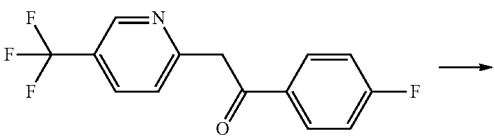

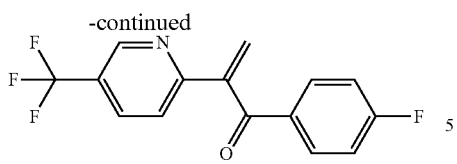

Acetic anhydride (2.87 g, 27.3 mmol) was added slowly to a stirring slurry of 1-(4-fluorophenyl)-2-[5-(trifluoromethyl)-2-pyridyl]ethanone (1.93 g 6.81 mmol) in N,N,N',N'-tetramethylmethanediamine (4.65 ml, 34.1 mmol) at 0° C. causing immediate dissolution. Thin layer chromatography showed complete conversion after 5 minutes and the mixture was partitioned between methyl tert-butyl (25 ml) ether and water (25 ml) by adding these solvents and separating the layers. The organic layer was washed with brine (20 ml), dried over sodium sulfate, filtered, and evaporated under reduced pressure to obtain the crude material which was purified by flash chromatography to give 1.4 g of 1-(4-fluorophenyl)-2-[5-(trifluoromethyl)-2-pyridyl]prop-2-en-1-one Step 3: Synthesis of 2-[1-[2-(4-fluorophenyl)oxiran-2-yl]cyclopropyl]-5-(trifluoromethyl)pyridine

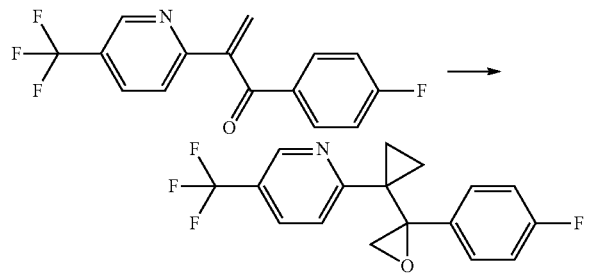

Sodium hydride (60% dispersion in mineral oil, 400 mg, 10 mmol) was placed under nitrogen then DMSO (20 ml) was added. Trimethylsulfonium iodide (2.20 g, 10 mmol) was added as a solid after 15 minutes, followed after a further 30 minutes by 1-(4-fluorophenyl)-2-[5-(trifluoromethyl)-2-pyridyl]prop-2-en-1-one (1.4 g, 4.7 mmol). The mixture was stirred at room temperature for 24 hours then diluted with ethyl acetate (50 ml) and washed with water (20 ml) and brine (20 ml). The organic phase was dried over magnesium sulphate, filtered and concentrated to give the crude compound. The product was purified by flash chromatography to give 2-[1-[2-(4-fluorophenyl)oxiran-2-yl]cyclopropyl]-5-(trifluoromethyl)pyridine which was still not pure however it was used as such in the next step.

Step 4: Synthesis of 1-(4-fluorophenyl)-2-(1,2,4-triazol-1-yl)-1-[1-[5-(trifluoromethyl)-2-pyridyl]cyclopropyl]ethanol

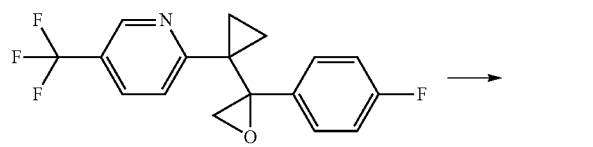

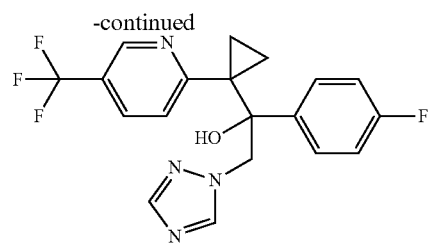

1H-1,2,4-triazole (256 mg, 3.71 mmol), potassium carbonate (375 mg, 3.71 mmol), dimethyl foramide (5 ml) and 2-[1-[2-(4-fluorophenyl)oxiran-2-yl]cyclopropyl]-5-(trifluoromethyl)pyridine (800 mg, 2.47 mmol) were mixed together and left to react 2 hours at 100 degrees. 20 ml of water and 20 ml of ethyl acetate were then added and the organic layer was separated. The organic phase was washed with brine (25 ml), dried over magnesium sulphate, filtered and the filtrate concentrated in vacuo to give the crude product. The orange oil was then absorbed onto silica and purified by flash chromatography using a gradient from cyclohexane 100% to neat ethyl acetate to yield 1-(4-fluorophenyl)-2-(1,2,4-triazol-1-yl)-1-[1-[5-(trifluoromethyl)-2-pyridyl]cyclopropyl]ethanol.

Table 1: This table discloses 32 specific compounds of formula (T-1) wherein $R^3$ is hydrogen and

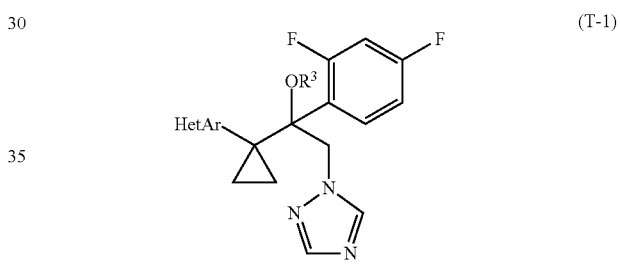

(T-1)

wherein HetAr is as defined below in the table (the dotted line shows where HetAr is attached to the molecule)

| No. | HetAr |
|---|---|
| 1.001 | 5-bromopyridin-2-yl |
| 1.002 | 5-chloropyridin-2-yl |
| 1.003 | 5-fluoropyridin-2-yl |
| 1.004 | 5-cyclopropylpyridin-2-yl |

-continued
| No. | HetAr |
|---|---|
| 1.005 | 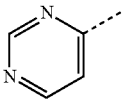 |
| 1.006 | 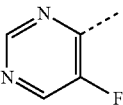 |
| 1.007 | 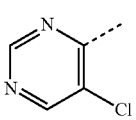 |
| 1.008 | 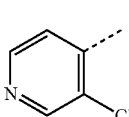 |
| 1.009 | 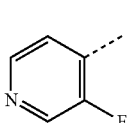 |
| 1.010 | 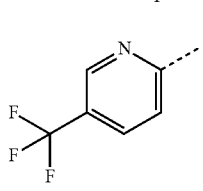 |
| 1.011 | 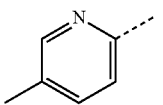 |
| 1.012 | 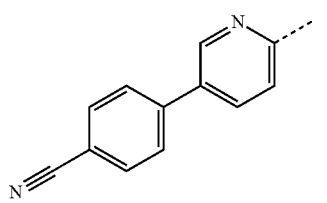 |
| 1.013 | 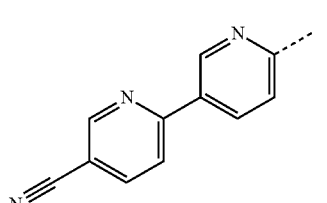 |
| 1.014 | 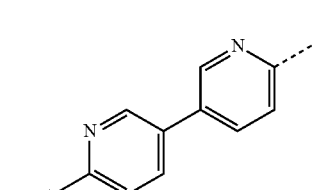 |
-continued
| No. | HetAr |
|---|---|
| 1.015 | 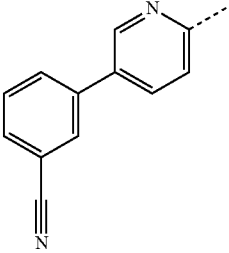 |
| 1.016 | 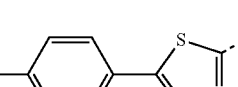 |
| 1.017 | 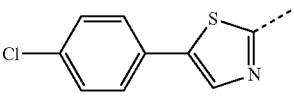 |
| 1.018 | 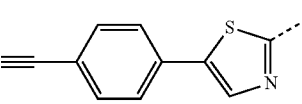 |
| 1.019 | 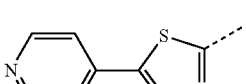 |
| 1.020 | 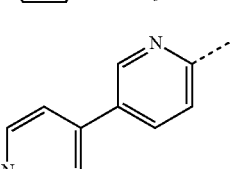 |
| 1.021 |  |
| 1.022 | 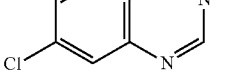 |
| 1.023 | 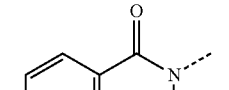 |
| 1.024 | 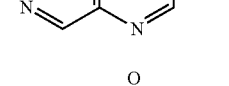 |

-continued

| No. | HetAr |
|---|---|
| 1.025 | 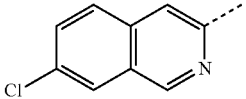 |
| 1.026 | 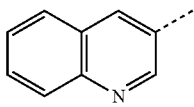 |
| 1.027 | 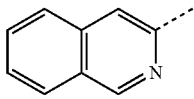 |
| 1.028 | 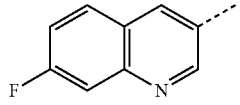 |
| 1.029 | 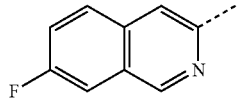 |
| 1.030 | 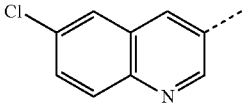 |
| 1.031 | 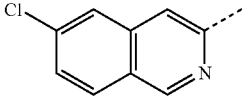 |
| 1.032 | 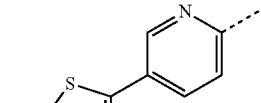 |

Table 2: This table discloses 32 specific compounds of the formula (T-1), wherein $R^3$ is methyl and HetAr is as defined in the Table 1.

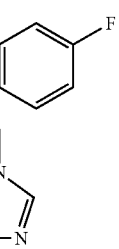
(T-1)

Table 3: This table discloses 32 specific compounds of formula (T-2), wherein $R^3$ is hydrogen and HetAr is as defined in the Table 1.

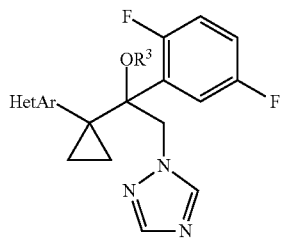
(T-2)

Table 4: This table discloses 32 specific compounds of the formula (T-2), wherein $R^3$ is methyl and HetAr is as defined in the Table 1.

Table 5: This table discloses 32 specific compounds of formula (T-3), wherein $R^3$ is hydrogen and HetAr is as defined in the Table 1.

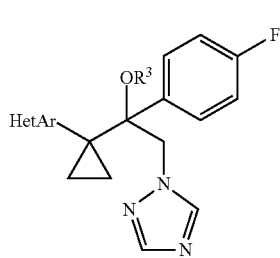
(T-3)

Table 6: This table discloses 32 specific compounds of the formula (T-3), wherein $R^3$ is methyl and HetAr is as defined in the Table 1.

Table 7: This table discloses 32 specific compounds of formula (T-4), wherein $R^3$ is hydrogen and HetAr is as defined in the Table 1.

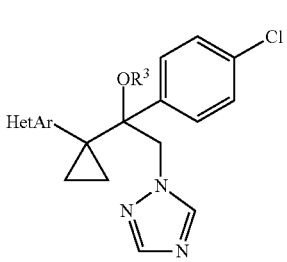
(T-4)

Table 8: This table discloses 32 specific compounds of the formula (T-4), wherein $R^3$ is methyl and HetAr is as defined in the Table 1.

Table 9: This table discloses 32 specific compounds of formula (T-5), wherein $R^3$ is hydrogen and HetAr is as defined in the Table 1.

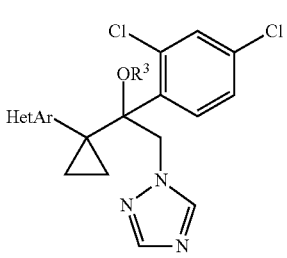
(T-5)

Table 10: This table discloses 32 specific compounds of the formula (T-5), wherein $R^3$ is methyl and HetAr is as defined in the Table 1.

Table 11: This table discloses 32 specific compounds of formula (T-6), wherein $R^3$ is hydrogen and HetAr is as defined in the Table 1.

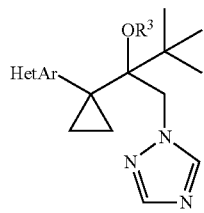

(T-6)

Table 12: This table discloses 32 specific compounds of the formula (T-6), wherein $R^3$ is methyl and HetAr is as defined in the Table 1.

Table 13: This table discloses 32 specific compounds of formula (T-7), wherein $R^3$ is hydrogen and HetAr is as defined in the Table 1.

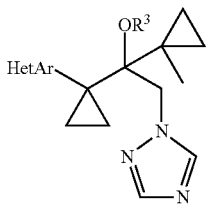

(T-7)

Table 14: This table discloses 32 specific compounds of the formula (T-7), wherein $R^3$ is methyl and HetAr is as defined in the Table 1.

Table 15: This table discloses 32 specific compounds of formula (T-8), wherein $R^3$ is hydrogen and HetAr is as defined in the Table 1.

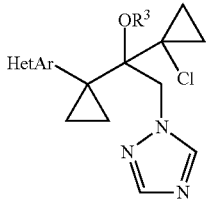

(T-8)

Table 16: This table discloses 32 specific compounds of the formula (T-8), wherein $R^3$ is methyl and HetAr is as defined in the Table 1.

Table 17: This table discloses 32 specific compounds of formula (T-9), wherein $R^3$ is hydrogen and HetAr is as defined in the Table 1.

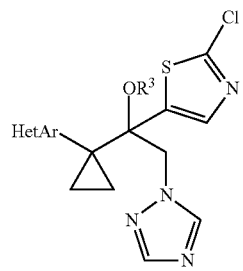

(T-9)

Table 18: This table discloses 32 specific compounds of the formula (T-9), wherein $R^3$ is methyl and HetAr is as defined in the Table 1.

Table 19: This table discloses 32 specific compounds of formula (T-10), wherein $R^3$ is hydrogen and HetAr is as defined in the Table 1.

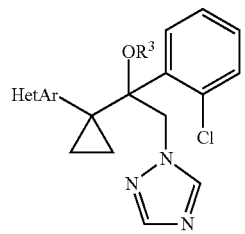

(T-10)

Table 20: This table discloses 32 specific compounds of the formula (T-10), wherein $R^3$ is methyl and HetAr is as defined in the Table 1.

Table 21: This table discloses 32 specific compounds of formula (T-11), wherein $R^3$ is hydrogen and HetAr is as defined in the Table 1.

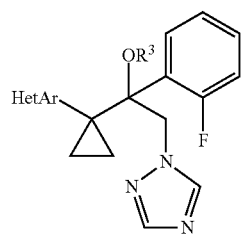

(T-11)

Table 22: This table discloses 32 specific compounds of the formula (T-11), wherein $R^3$ is methyl and HetAr is as defined in the Table 1.

Table T1 shows selected LCMS data and retention times/molecular ion as examples compounds similar to the one described in Tables 1 to 22.

The analytical method used is described here below:

ACQUITY SQD Mass Spectrometer from Waters (Single quadrupole mass spectrometer)

Ionisation method: Electrospray

Polarity: positive ions

Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400
Method Waters ACQUITY UPLC with the following HPLC gradient conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 80 | 20 | 1.5 |
| 0.1 | 75 | 25 | 1.5 |
| 0.2 | 70 | 30 | 0.75 |
| 1.20 | 0 | 100 | 0.75 |
| 1.40 | 0 | 100 | 0.75 |
| 1.45 | 80 | 20 | 0.75 |

Type of column: Waters ACQUITY UPLC HSS T3; Column length: 30 mm; Internal diameter of column: 2.1 mm; Particle Size: 1.8 micron; Temperature: 60° C.

TABLE T1

Melting point data and/or retention times for compounds:

| Entry | STRUCTURE | RT (min) | [M + H]+ (measured) |
|---|---|---|---|
| 1 | 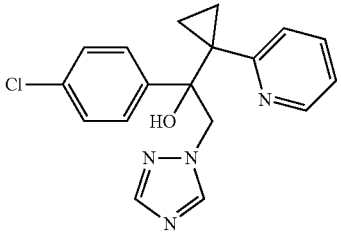 [SMILES: OC(Cn1cncn1)(c1ccc(Cl)cc1)C1(c2ccccn2)CC1] | 0.71 | 341 |
| 2 | 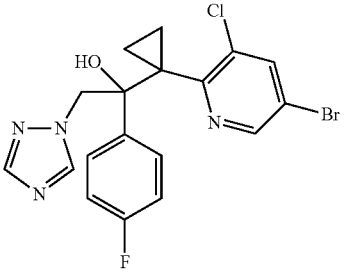 [SMILES: OC(Cn1cncn1)(c1ccc(F)cc1)C1(c2ncc(Br)cc2Cl)CC1] | 1.07 | 439 |
| 3 | 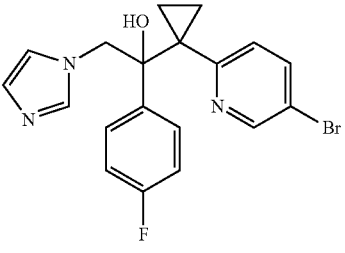 [SMILES: OC(Cn1ccnc1)(c1ccc(F)cc1)C1(c2ccc(Br)cn2)CC1] | 0.74 | 404 |
| 4 | 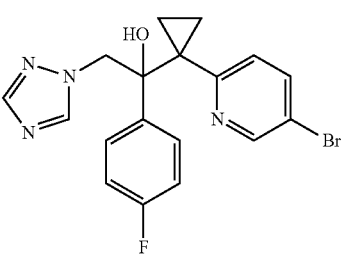 [SMILES: OC(Cn1cncn1)(c1ccc(F)cc1)C1(c2ccc(Br)cn2)CC1] | 0.97 | 405 |

TABLE T1-continued

Melting point data and/or retention times for compounds:

| Entry | STRUCTURE | RT (min) | [M + H]+ (measured) |
|---|---|---|---|
| 5 | 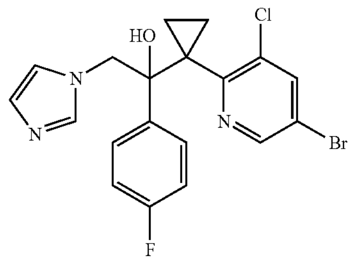 [SMILES: OC(Cn1ccnc1)(c1ccc(F)cc1)C1(c2ncc(Br)cc2Cl)CC1] | 0.82 | 438 |
| 6 | 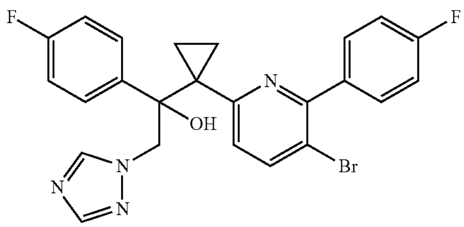 [SMILES: OC(Cn1cncn1)(c1ccc(F)cc1)C1(c2ccc(Br)c(-c3ccc(F)cc3)n2)CC1] | 1.11 | 497 |
| 7 | 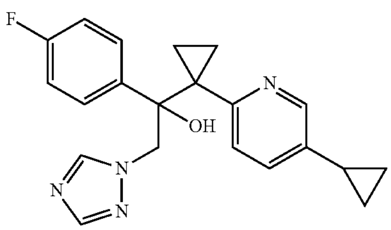 [SMILES: OC(Cn1cncn1)(c1ccc(F)cc1)C1(c2ccc(C3CC3)cn2)CC1] | 0.75 | 365 |
| 8 | 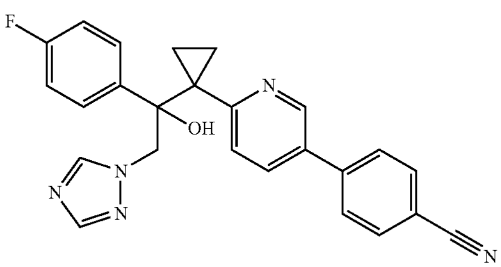 [SMILES: N#Cc1ccc(-c2ccc(C3(C(O)(Cn4cncn4)c4ccc(F)cc4)CC3)nc2)cc1] | 0.96 | 426 |
| 9 | 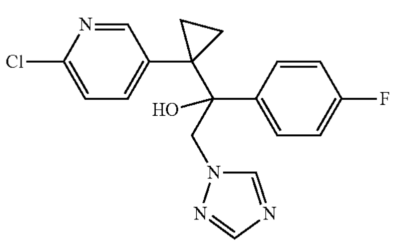 [SMILES: OC(Cn1cncn1)(c1ccc(F)cc1)C1(c2ccc(Cl)nc2)CC1] | 0.89 | 359 |
| 10 | 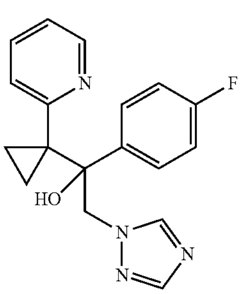 [SMILES: OC(Cn1cncn1)(c1ccc(F)cc1)C1(c2ccccn2)CC1] | 0.62 | 325 |

TABLE T1-continued

Melting point data and/or retention times for compounds:

| Entry | STRUCTURE | RT (min) | [M + H]+ (measured) |
|---|---|---|---|
| 11 | 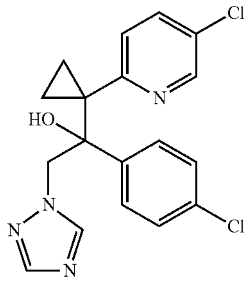 [SMILES: OC(Cn1cncn1)(c1ccc(Cl)cc1)C1(c2ccc(Cl)cn2)CC1] | 1.00 | 375 |
| 12 | 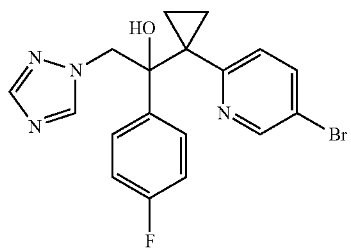 [SMILES: OC(Cn1cncn1)(c1ccc(F)cc1)C1(c2ccc(Br)cn2)CC1] | 0.84 | 350 |
| 13 | 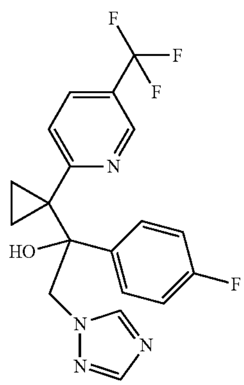 [SMILES: OC(Cn1cncn1)(c1ccc(F)cc1)C1(c2ccc(C(F)(F)F)cn2)CC1] | 0.98 | 393 |
| 14 | 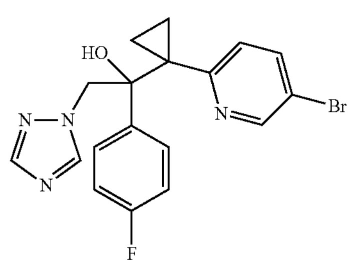 [SMILES: OC(Cn1cncn1)(c1ccc(F)cc1)C1(c2ccc(Br)cn2)CC1] | 0.94 | 359 |
| 15 | 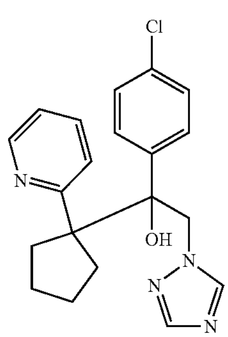 [SMILES: OC(Cn1cncn1)(c1ccc(Cl)cc1)C1(c2ccccn2)CCCC1] | 0.93 | 369 |

TABLE T1-continued

Melting point data and/or retention times for compounds:

| Entry | STRUCTURE | RT (min) | [M + H]+ (measured) |
|---|---|---|---|
| 16 | (structure) | 1.08 | 389 |
| 17 | (structure) | 1.04 | 417 |
| 18 | (structure) | 1.17 | 499 |
| 19 | (structure) | 1.17 | 467 |

FORMULATION EXAMPLES FOR COMPOUNDS OF FORMULA (I)

Example F-1.1 to F-1.2

Emulsifiable Concentrates

| Components | F-2.1 | F-2.2 |
|---|---|---|
| A compound selected from the Tables 2 to 22 and Table T1 | 25% | 50% |
| calciumdodecylbenzenesulfonate | 5% | 6% |

-continued

| Components | F-2.1 | F-2.2 |
|---|---|---|
| castoroilpolyethyleneglycolether (36molethylenoxyunits) | 5% | — |
| tributylphenolpolyethyleneglycolether (30molethylenoxyunits) | — | — |
| cyclohexanone | — | 20% |
| xylenemixture | 65% | 20% |

Emulsions of any desired concentration can be prepared by diluting such concentrates with water.

Example F-2

Emulsifiable Concentrate

| Components | F-2 |
| --- | --- |
| A compound selected from the Tables 2 to 22 and Table T1 | 10% |
| octylphenolpolyethyleneglycolether (4 to 5 mol ethylenoxy units) | 3% |
| Calcium dodecylbenzenesulfonate | 3% |
| Castoroilpolyglycolether (36 mol ethylenoxy units) | 4% |
| cyclohexanone | 30% |
| xylenemixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
| --- | --- | --- | --- | --- |
| A compound selected from the Tables 2 to 22 and Table T1 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
| --- | --- | --- | --- | --- |
| A compound selected from the Tables 2 to 22 and Table T1 | 5% | 10% | 8% | 21% |
| Kaolin | 94% | — | 79% | 54% |
| highly dispersed silicic acid | 1% | — | 13% | 7% |
| Attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
| --- | --- | --- |
| A compound selected from the Tables 2 to 22 and Table T1 | 2% | 5% |
| highly dispersed silicic acid | 1% | 5% |
| Talcum | 97% | — |
| Kaolin | — | 90% |

Ready for use dusts are obtained by intimately mixing all components.

Examples F-6.1 to F-6.3

Wettable Powders

| Components | F-6.1 | F-6.2 | F-6.3 |
| --- | --- | --- | --- |
| A compound selected from the Tables 2 to 22 and Table T1 | 25% | 50% | 75% |
| sodium lignin sulfonate | 5% | 5% | — |
| sodium lauryl sulphate | 3% | — | 5% |
| sodium diisobutylnaphthalene sulfonate | 6% | 10% | — |
| octylphenolpolyethylene glycol ether (7 to 8 mol ethylenoxy units) | 2% | — | — |
| highly dispersed silicic acid | 5% | 10% | 10% |
| Kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| Components | F-7 |
| --- | --- |
| A compound selected from the Tables 2 to 22 and Table T1 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

These examples illustrate the fungicidal properties of the compounds described in table T1.

Biological Example 1

Fungicidal Activity Against *Blumeria Graminis* f. sp. *Tritici* (*Erysiphe Graminis* f. sp. *Tritici*)/Wheat/Leaf Disc Preventative (Powdery Mildew on Wheat)

Wheat leaf segments cv. Kanzler were placed on agar in a multiwell plate (24-well format) and sprayed with the formulated test compound diluted in water. The leaf disks were inoculated by shaking powdery mildew infected plants above the test plates 1 day after application. The inoculated leaf disks were incubated at 20° C. and 60% rh under a light regime of 24 h darkness followed by 12 h light/12 h darkness in a climate chamber and the activity of a compound was assessed as percent disease control compared to untreated when an appropriate level of disease damage appears on untreated check leaf segments (6-8 days after application).

Compounds (from table T1) 1, 2, 3, 4, 5, 6, 7, 8, 9, 10, 11, 12, 13, 14, 15, 16, 17, 18 and 19 at 200 ppm give at least 80% disease control in this test when compared to untreated control leaf disks under the same conditions, which show extensive disease development.

Biological Example 2

Fungicidal Activity Against *Puccinia Recondita* f. sp. *Tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (7-9 days after application).

Compounds (from table T1) 1, 2, 3, 4, 5, 6, 7, 8, 9, 10, 11, 12, 13, 14, 15, 16 and 17 at 200 ppm give at least 80% disease control in this test when compared to untreated control leaf disks under the same conditions, which show extensive disease development.

Biological Example 3

Fungicidal Activity Against *Puccinia Recondita* f. sp. *Tritici*/Wheat/Leaf Disc Curative (Brown Rust)

Wheat leaf segments are placed on agar in multiwell plates (24-well format). The leaf disks are then inoculated with a spore suspension of the fungus. One day after inoculation the test solution is applied. After appropriate incubation the activity of a compound is assessed 8 dpi (days after inoculation) as curative fungicidal activity. Dose range: 200-22 ppm.

Compounds (from table T1) 1, 2, 3, 4, 5, 6, 7, 8, 9, 10, 11, 12, 13, 14, 15, 16 and 17 at 200 ppm give at least 80% disease control in this test when compared to untreated control leaf disks under the same conditions, which show extensive disease development.

Biological Example 4

Fungicidal Activity Against *Pyrenophora Teres*/Barley/Leaf Disc Preventative (Net Blotch)

Barley leaf segments cv. Hasso were placed on agar in a multiwell plate (24-well format) and sprayed with the formulated test compound diluted in water. The leaf segments were inoculated with a spore suspension of the fungus 2 days after application. The inoculated leaf segments were incubated at 20° C. and 65% rh under a light regime of 12 h light/12 h darkness in a climate cabinet and the activity of a compound was assessed as disease control compared to untreated when an appropriate level of disease damage appears in untreated check leaf segments (5-7 days after application).

Compounds (from table T1) 3, 4, 7, 10, 11, 13 and 14 at 200 ppm give at least 80% disease control in this test when compared to untreated control leaf disks under the same conditions, which show extensive disease development.

Biological Example 5

Fungicidal Activity Against *Botryotinia Fuckeliana* (*Botrytis Cinerea*)/Liquid Culture (Gray Mould)

Conidia of the fungus from cryogenic storage were directly mixed into nutrient broth (Vogels broth). After placing a (DMSO) solution of test compound into a microtiter plate (96-well format), the nutrient broth containing the fungal spores was added. The test plates were incubated at 24° C. and the inhibition of growth was determined photometrically 3-4 days after application.

Compounds (from table T1) 1, 4, 11 and 17 at 200 ppm give at least 80% disease control in this test when compared to untreated control leaf disks under the same conditions, which show extensive disease development.

Biological Example 6

Fungicidal Activity Against *Mycosphaerella Arachidis* (*Cercospora Arachidicola*)/Liquid Culture (Early Leaf Spot)

Conidia of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically 4-5 days after application.

Compounds (from table T1) 1, 2, 4, 6, 7, 8, 9, 10, 11, 13, 14, 15, 16, 17, 18 and 19 at 200 ppm give at least 80% disease control in this test when compared to untreated control leaf disks under the same conditions, which show extensive disease development.

Biological Example 7

Fungicidal Activity Against *Mycosphaerella Graminicola* (*Septoria Tritici*)/Liquid Culture (*Septoria* Blotch)

Conidia of the fungus from cryogenic storage were directly mixed into nutrient broth (PDB potato dextrose broth). After placing a (DMSO) solution of test compound into a microtiter plate (96-well format), the nutrient broth containing the fungal spores was added. The test plates were incubated at 24° C. and the inhibition of growth was determined photometrically 4-5 days after application.

Compounds (from table T1) 1, 2, 7, 8, 9, 10, 11, 12, 13, 14, 15, 16, 17, 18 and 19 at 200 ppm give at least 80% disease control in this test when compared to untreated control leaf disks under the same conditions, which show extensive disease development.

Biological Example 8

Fungicidal Activity Against *Gaeumannomyces Graminis*/Liquid Culture (Take-All of Cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores is added. The test plates were incubated at 24° C. and the inhibition of growth was determined photometrically 4-5 days after application.

Compounds (from table T1) 1, 2, 8, 11 and 17 at 200 ppm give at least 80% disease control in this test when compared to untreated control leaf disks under the same conditions, which show extensive disease development.

Biological Example 9

Fungicidal Activity Against *Thanatephorus Cucumeris* (*Rhizoctonia Solani*)/Liquid Culture (Foot Rot, Damping-Off)

Mycelia fragments of a newly grown liquid culture of the fungus were directly mixed into nutrient broth (PDB potato dextrose broth). After placing a (DMSO) solution of the test compounds into a microtiter plate (96-well format), the nutrient broth containing the fungal material was added. The test plates were incubated at 24° C. and the inhibition of growth was determined photometrically 3-4 days after application. Compounds (from table T1) 1, 2, 4, 7, 8, 10, 11, 13, 14 and 17 at 200 ppm give at least 80% disease control in this test when compared to untreated control leaf disks under the same conditions, which show extensive disease development.

Biological Example 10

Fungicidal Activity Against *Sclerotinia Sclerotiorum*/Liquid Culture (White Mold, etc.):

Mycelial fragments of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hrs at 620 nm.

Compounds (from table T1) 2, 8 and 11 at 200 ppm give at least 80% disease control in this test when compared to untreated control leaf disks under the same conditions, which show extensive disease development.

The invention claimed is:
1. A compound of formula (I)

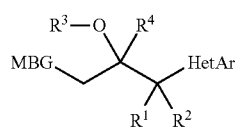

(I)

wherein
MBG is optionally substituted tetrazolyl, optionally substituted triazolyl, optionally substituted oxazolyl, optionally substituted thiazolyl, or optionally substituted imidazolyl;
HetAr is a carbon attached pyridyl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form an optionally substituted 3- to 8-membered ring, optionally containing an oxygen, sulphur or nitrogen atom;
$R^3$ is hydrogen, alkyl, —Si($R^5$)$_3$, —P(O)(OH)$_2$, —CH$_2$—O—P(O)(OH)$_2$, —C(O)-alkyl, —C(O)—O-alkyl, or —C(O)—N-alkyl;
$R^4$ is aryl, heteroaryl, alkyl or cycloalkyl each optionally substituted with 0, 1, 2 or 3 independent $R^6$;
$R^5$ is independently alkyl or aryl;
$R^6$ is independently cyano, haloalkyl, hydroxy, alkoxy, halogen, or haloalkoxy;
or an agronomically acceptable salt, stereoisomer, diastereoisomer, enantiomer, tautomer, atriopisomer or N-oxide thereof.

2. A compound of formula (I) according to claim 1 characterized in that
MBG is a triazolyl, a tetrazolyl, a triazolyl, an oxazolyl, a thiazolyl, or a imidazolyl;
HetAr is a carbon attached pyridyl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^1$ and $R^2$ together with the carbon atoms to which they are attached form a 3- to 6-membered ring optionally substituted with 0, 1, 2 or 3 independent $R^6$ and optionally containing an oxygen, sulphur or nitrogen atom;
$R^3$ is hydrogen or alkyl;
$R^4$ is aryl or heteroaryl, each optionally substituted with 0, 1, 2 or 3 independent $R^6$;
$R^6$ is independently cyano, $C_1$-$C_6$haloalkyl, hydroxy, $C_1$-$C_6$alkoxy, halogen, or $C_1$-$C_6$haloalkoxy.

3. A compound of formula (I) according to claim 1 characterized in that
MBG is a triazolyl or a imidazolyl;
HetAr is a carbon attached pyridyl wherein the substituents are selected from the group consisting of halogen, $C_1$-$C_4$haloalkyl, $C_1$-$C_4$haloalkoxy, $C_3$-$C_8$cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;
$R^3$ is hydrogen or $C_1$-$C_4$alkyl;
$R^4$ is aryl or heteroaryl, each optionally substituted with 1 or 2 independent $R^6$;
$R^6$ is independently cyano, $C_1$-$C_6$haloalkyl, halogen or $C_1$-$C_6$haloalkoxy.

4. A compound of formula (I) according to claim 1 characterized in that
MBG is a triazolyl or a imidazolyl;
HetAr is a carbon attached pyridyl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy
$R^3$ is hydrogen or $C_1$-$C_4$alkyl;
$R^4$ is aryl or heteroaryl, each optionally substituted with 1 or 2 independent $R^6$;
$R^6$ is independently cyano, $C_1$-$C_6$haloalkyl, halogen or $C_1$-$C_6$haloalkoxy.

5. A compound of formula (I) according to claim 1 characterized in that

MBG is a triazolyl;

HetAr is a carbon attached pyridyl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form a 3- to 6-membered ring optionally substituted with 0, 1, 2 or 3 independent $R^6$ and optionally containing an oxygen;

$R^3$ is hydrogen or methyl;

$R^4$ is aryl or heteroaryl, each optionally substituted with 1 or 2 independent $R^6$;

$R^6$ is independently $C_1$-$C_4$haloalkyl, fluorine, chlorine, or $C_1$-$C_4$haloalkoxy.

6. A compound of formula (I) according to claim 1 characterized in that

MBG is a triazolyl;

HetAr is a carbon attached pyridyl wherein the substituents are selected from the group consisting of halogen, $C_1$-$C_4$haloalkyl, $C_1$-$C_4$haloalkoxy, $C_3$-$C_8$ cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form a 3- to 6-membered ring optionally substituted with 0, 1, 2 or 3 independent $R^6$ and optionally containing an oxygen;

$R^3$ is hydrogen or methyl;

$R^4$ is aryl, optionally substituted with 1 or 2 independent $R^6$;

$R^6$ is independently $C_1$-$C_4$haloalkyl, fluorine, chlorine, or $C_1$-$C_4$haloalkoxy.

7. A method of controlling or preventing infestation of useful plants by phytopathogenic microorganisms, wherein a compound of formula (I) as defined in claim 1 or a composition comprising a compound of formula (I) as defined in claim 1 as active ingredient, is applied to the plants, to parts thereof or the locus thereof.

8. A composition for controlling and protecting against phytopathogenic microorganisms, comprising a compound of formula (I) as defined in claim 1 and at least one auxiliary.

9. A method of controlling phytopathogenic diseases on useful plants or plant propagation material thereof, which comprises applying to said plant propagation material a fungicidally effective amount of a plant propagation material protecting composition comprising a compound of formula (I) as defined in claim 1, together with a suitable carrier therefor.

10. A composition comprising a fungicidally effective amount of a compound of formula (I) as defined in claim 1, optionally comprising at least one additional active ingredient.

11. A compound of formula (I) according to claim 1 characterized in that MBG is a triazolyl or imidazolyl;

HetAr is pyrid-2-yl wherein the substituents are selected from the group consisting of halogen, cyano, $C_1$-$C_4$haloalkyl, $C_1$-$C_4$haloalkoxy, $C_3$-$C_8$cycloalkyl or phenyl optionally further substituted by halogen, cyano, nitro, hydroxy, $C_1$-$C_4$alkyl, $C_1$-$C_4$haloalkyl, $C_1$-$C_4$alkoxy, $C_1$-$C_4$haloalkoxy;

$R^1$ and $R^2$ together with the carbon atoms to which they are attached form an optionally substituted cyclopropyl or cyclobutanyl;

$R^3$ is hydrogen or methyl;

$R^4$ is aryl, optionally substituted with 1, 2 independent $R^6$; and $R^6$ is independently $C_1$-$C_4$haloalkyl, fluorine, chlorine, $C_1$-$C_4$haloalkoxy.

12. A compound of formula (I) according to claim 1 characterized in that MBG is a triazolyl or imidazolyl;

HetAr is pyrid-2-yl wherein the substituents are selected from the group consisting of halogen, cyano, $C_1$-$C_4$haloalkyl, $C_3$-$C_8$ cycloalkyl or phenyl optionally further substituted by halogen, $C_1$-$C_4$haloalkyl, $C_1$-$C_4$haloalkoxy;

$R^1$ and $R^2$ together with the carbon atoms to which they are attached form an optionally substituted 3- to 4-membered carbocyclic ring;

$R^3$ is hydrogen or methyl;

$R^4$ is aryl, optionally substituted with 1, 2 independent $R^6$; and $R^6$ is independently $C_1$-$C_4$haloalkyl, fluorine, chlorine, $C_1$-$C_4$haloalkoxy.

\* \* \* \* \*